United States Patent
Webber

(10) Patent No.: US 11,934,043 B2
(45) Date of Patent: Mar. 19, 2024

(54) MYOPIA CONTROL LENS AND RELATED METHODS

(71) Applicant: CooperVision International Limited, Fareham (GB)

(72) Inventor: Martin Webber, Southampton (GB)

(73) Assignee: COOPERVISION INTERNATIONAL LIMITED, Fareham (GB)

( * ) Notice: Subject to any disclaimer, the term of this patent is extended or adjusted under 35 U.S.C. 154(b) by 299 days.

(21) Appl. No.: 17/228,755

(22) Filed: Apr. 13, 2021

(65) Prior Publication Data

US 2021/0341752 A1    Nov. 4, 2021

Related U.S. Application Data

(60) Provisional application No. 63/017,940, filed on Apr. 30, 2020.

(51) Int. Cl.
*G02C 7/04*    (2006.01)

(52) U.S. Cl.
CPC ........... *G02C 7/04* (2013.01); *G02C 2202/24* (2013.01)

(58) Field of Classification Search
CPC ........ G02C 7/04; G02C 2202/24; G02C 7/06; G02C 7/042; G02C 7/02; G02C 7/022; A61F 2/1618; B29D 11/00038; G02B 1/041; G02B 1/043
See application file for complete search history.

(56) References Cited

U.S. PATENT DOCUMENTS

| | | | |
|---|---|---|---|
| 7,766,478 B2 | 8/2010 | Phillips |
| 7,832,859 B2 | 11/2010 | Phillips |
| 8,240,847 B2 | 8/2012 | Holden et al. |
| 8,950,860 B2 | 2/2015 | Tse et al. |
| 9,594,259 B2 | 3/2017 | Brennan et al. |
| 9,829,722 B2 | 11/2017 | Tse et al. |
| RE47,006 E | 8/2018 | To et al. |
| 10,061,143 B2 | 8/2018 | Brennan et al. |
| 10,268,050 B2 | 4/2019 | To et al. |
| 10,416,476 B2 | 9/2019 | Lin et al. |

(Continued)

FOREIGN PATENT DOCUMENTS

| | | |
|---|---|---|
| EP | 0622653 | * 11/1994 |
| EP | 0622653 A1 | 11/1994 |

(Continued)

OTHER PUBLICATIONS

International Search Report and Written Opinion issued in corresponding International Patent Application No. PCT/GB2021/051039 dated Aug. 9, 2021 (16 pages).

(Continued)

*Primary Examiner* — Balram T Parbadia
*Assistant Examiner* — Gabriel A Sanz
(74) *Attorney, Agent, or Firm* — Kilyk & Bowersox, P.L.L.C.

(57) ABSTRACT

An ophthalmic lens for myopia control. A first surface of the lens varies across the lens to form a first surface power map. A second surface of the lens varies across the lens to form a second surface power map. Each of the first and second surface power maps comprise a spiral. The spirals formed by the first and second surface power maps twist in opposing directions. Related methods are also described.

18 Claims, 7 Drawing Sheets

(56) References Cited

U.S. PATENT DOCUMENTS

| | | | |
|---|---|---|---|
| 10,429,670 B2 | 10/2019 | Newman | |
| 2003/0117577 A1 | 6/2003 | Jones et al. | |
| 2005/0068489 A1* | 3/2005 | Hall | G02C 7/043 351/159.1 |
| 2009/0048670 A1 | 2/2009 | Grierson et al. | |
| 2011/0273663 A1* | 11/2011 | Pugh | G02C 7/04 425/542 |
| 2012/0062836 A1* | 3/2012 | Tse | G02C 7/042 351/159.41 |
| 2014/0211313 A1 | 7/2014 | Dobschal | |
| 2014/0293426 A1 | 10/2014 | Dobschal | |
| 2016/0377884 A1 | 12/2016 | Lau et al. | |
| 2017/0115509 A1 | 4/2017 | Brennan et al. | |
| 2018/0275427 A1 | 9/2018 | Lau et al. | |
| 2019/0212580 A1 | 7/2019 | To et al. | |
| 2022/0050355 A1* | 2/2022 | Geday | G02B 3/08 |

FOREIGN PATENT DOCUMENTS

| | | |
|---|---|---|
| EP | 2761359 A1 | 8/2014 |
| JP | 2009529376 A | 8/2009 |
| WO | 02061497 A1 | 8/2002 |
| WO | 2009012789 A1 | 1/2009 |
| WO | 2012156081 A1 | 11/2012 |
| WO | 2013001299 A1 | 1/2013 |
| WO | 2015004881 A1 | 1/2015 |
| WO | 2020260679 A1 | 12/2020 |

OTHER PUBLICATIONS

Search Report issued in corresponding United Kingdom Patent Application No. GB2106175.9 dated Oct. 6, 2021 (3 pages).

U.S. Appl. No. 17/228,752, filed Apr. 13, 2021 (39 pages).

U.S. Appl. No. 17/228,757, filed Apr. 13, 2021 (45 pages).

Office Action issued in corresponding Japanese Patent Application No. 2022-564027 dated Sep. 26, 2023 (9 pages)(with partial English translation).

* cited by examiner

MYOPIA CONTROL LENS AND RELATED METHODS

This application claims the benefit under 35 U.S.C. § 119(e) of prior U.S. Provisional Patent Application No. 63/017,940, filed Apr. 30, 2020, which is incorporated in its entirety by reference herein.

TECHNICAL FIELD

The present invention concerns ophthalmic lenses and methods for reducing the progression of myopia (i.e., myopia control). More particularly, but not exclusively, this invention concerns an ophthalmic lens for myopia control having a first surface and a second surface, the first and second surfaces providing respective first and second surface power maps, wherein the first and second surface power maps comprise counter-rotating spirals. The invention also concerns methods of making and using such lenses.

BACKGROUND

A myopia control lens is an ophthalmic lens which attempts to control the progression of a wearer's myopia. This is typically achieved by subdividing the ophthalmic lens into a plurality of regions. Regions in a first subset of the plurality of regions are provided with a first lens power, corresponding to a first focussing distance (for example to correct distance vision for an unaccommodated eye). Regions in a second subset of the plurality of regions have a second lens power selected to provide a myopic defocus.

In the case of contact lenses for myopia control, the plurality of regions are typically formed as concentric circles centred on the optical axis of the contact lens, with the concentric circles alternating between the first lens power, providing corrected vision, and the second lens power, providing the myopic defocus. Thus, the power map of a myopia control contact lens comprises at least two alternating concentric circles of a first and second lens power. However, in lower light conditions the pupil of the wearer's eye dilates in order to provide a larger aperture for incident light, increasing the amount of light received into the eye and thereby providing improved low-light vision. As conditions brighten, the pupil constricts to provide a smaller aperture and thereby limit the amount of light received into the eye. As the wearer's pupil dilates and constricts, the number of the concentric rings on the contact lens which are positioned across the wearer's entrance pupil will also vary. As the pupil dilates, a greater number of the concentric rings will be positioned across the wearer's entrance pupil. Likewise, as the pupil constricts, fewer of the concentric rings will be positioned across the wearer's entrance pupil. Because the concentric rings alternate between the first lens power and the second lens power, the amount of second lens power providing the myopic defocus which is positioned across the wearer's entrance pupil will vary as the wearer's pupil constricts and dilates. In some cases, the pupil may even constrict to the extent that none of the second lens power providing the myopic defocus is positioned across the wearer's entrance pupil, resulting in a failure of the lens to provide effective control of myopia progression.

In addition to varying pupil size, lens decentration and, in the case of a spectacle lens, movement of the wearer's eye behind the lens can also impair the ability of a lens to provide effective myopia control. Each of the above factors can cause variation in the ratio of the first and second lens powers.

Several lens designs have been described for reducing the progression of myopia. MISIGHT (CooperVision) is the first of such contact lenses to receive regulatory approval in the United States. MISIGHT contact lenses are dual focus contact lenses that provide a myopically defocused image at both near and far viewing distances. The dual focus design includes a central distance correction zone circumscribed by alternating rings of different optical powers. Another concentric ring lens design is referred to as Defocus Incorporated Soft Contact (DISC) lenses and was developed by Hong Kong Polytechnic University (HKPU) and is being commercialized by Vision Science and Technology Co. Ltd. HKPU and Hoya Vision Care have developed a myopia control spectacle lens referred to as Defocus Incorporated Multiple Segments (DIMS) glasses under the name MyoSmart (Hoya). In addition, another spectacle lens for myopia control has been developed by Sightglass Vision. Examples of myopia control ophthalmic lenses have been described in the patent literature, including the following: U.S. Pat. Nos. 7,766,478; 7,832,859; 8,240,847; USRE47006; 8,950,860; 9,594,259; 9,829,722; 10,061,143; 10,416,476; 10,268,050; 10,429670; US20190212580; US20180275427; US20160377884; and US20170115509.

It is important to ensure that myopia control lenses reduce the formation of additional, unwanted images. If parts of a lens which provide myopic defocus also form an additional image, there is a possibility that the wearer of the lens may simply "tune" into the additional image, rather than exercising his or her eye's ability to accommodate. This is undesirable. It will be appreciated that, where a lens design includes separate regions, only some of which are dedicated to myopia control, the limitations above on preventing unintended image formation apply to those regions dedicated to myopia control, not to the whole of the lens.

The present invention seeks to mitigate the above-mentioned problems. Alternatively or additionally, the present invention seeks to provide an improved ophthalmic lens for myopia control.

SUMMARY

The present invention provides, according to a first aspect, an ophthalmic lens for controlling myopia progression. A first surface of the ophthalmic lens is shaped to form a first surface power map. A second surface of the ophthalmic lens is shaped to form a second surface power map. The first surface power map comprises a spiral. The second surface power map also comprises a spiral. The spirals formed by the first and second surface power maps twist in opposing directions.

The overall power map of the contact lens is determined by the superposition of the first surface power map and the second surface power map. The spirals provided by the first and second surface power maps twist in opposing directions. Thus, the first and second surface power maps can be said to comprise counter-rotating spirals. The superposition of the two counter-rotating spirals formed by the first surface power map and the second surface power map results in a lens power map which approximates a pseudo-dartboard pattern of alternating annular rings or multiple segments of defocus. The overall lens power map varies between a first lens power, which provides distance vision, and a second lens power, which provides a myopic defocus. As the ophthalmic lens is intended as a myopia control lens, a wearer of the ophthalmic lens will generally be between the ages of approximately 5 years and 18 years and, therefore, the wearer's eyes are very likely able to accommodate. It will therefore be appreciated that, although the first lens power is selected for distance vision, the wearer may also view near distances through those parts of the lens providing the first lens power due to the wearer's ability to accommodate.

A contact lens having a power map which approximates a pseudo-dartboard pattern can be effective in providing myopia control. Such a lens power map also provides a more stable ratio of lens powers (i.e. the ratio of the lens powers providing myopic defocus to those providing distance vision focussing) in the presence of changes in the pupil size of the wearer. As light conditions change, the wearer's pupil will dilate and constrict in order to regulate the amount of light received into the eye. As conditions brighten, the pupil constricts to reduce the amount of light allowed into the eye. As conditions darken, the pupil dilates to allow more light into the eye. Some myopia control contact lenses of the prior art use alternating concentric rings of a first lens power providing distance vision focussing and a second lens power providing a myopic defocus, for example a central circle of the first lens power surrounded by a peripheral circle of the second lens power. These contact lenses suffer from variation in the ratio of lens powers (i.e. the ratio of lens powers providing a myopic defocus to those providing distance vision focussing) positioned across the wearer's entrance pupil as the wearer's pupil dilates and constricts. These variations can impair the lens' ability to provide effective myopia control. Thus, contact lenses according to the present invention can provide effective myopia control in the presence of varying pupil dilation.

A spiral power map as disclosed herein can provide a constant ratio of lens powers providing myopic defocussing to those providing distance focussing across the full range of diameters including the spiral. Thus, a contact lens having a spiral power map can maintain either a substantially constant ratio (where the spiral cover the whole of the lens) or a monotonically varying ratio (where the spiral covers only a radial sub-portion of the lens) of focus and myopic defocus as the pupil constricts or dilates. The pseudo-dartboard pattern provided by the superposition of two counter-rotating spirals also provides this same benefit. Thus, a contact lens having a pseudo-dartboard power map reduces variations in the ratio of myopic defocussing to distance focussing in the presence of variable lighting conditions.

It will be appreciated by the skilled person that, where the power map varies smoothly (for example, as a sinusoid), the power map will comprise lens powers other than simply a first lens power associated with distance vision focussing and a second lens power associated with myopic defocus. In such a case, the power map will also comprise regions having lens powers between the first and second powers. It will be appreciated that this does not affect or diminish the advantage described above of providing a consistent and stable variation in the ratio of focus and myopic defocus positioned across the wearer's entrance pupil. It will be appreciated by the skilled person that this advantage is derived from that fact that, for spiral and pseudo-dartboard power maps, the composition of lens powers at a particular radius does not vary according to a radial distance from the optical axis of the lens.

According to a second aspect of the invention there is also provided a method of manufacturing an ophthalmic lens for myopia control. The method comprises operating a lathe to shape first and second surfaces of at least one of: a lens, a mould for a lens, or an insert for manufacturing a mould for a lens. The first surface is shaped such that it forms a first surface power map. The second surface is shaped such that it forms a second surface power map. The first surface power map and the second surface power map each comprise a spiral. The spirals formed by the first surface power map and the second surface power map twist in opposing directions.

According to a third aspect of the invention there is also provided a method of using the ophthalmic lens described herein. The methods may be effective in reducing progression of a refractive error, such as reducing the progression of myopia or hyperopia. The methods include a step of providing the ophthalmic lenses to a person whose eyes are able to accommodate. The method may include a step of providing the ophthalmic lenses to a person that is from about 5 years old to about 18 years old. The providing may be performed by an eye care practitioner, such as an optician or optometrist. Alternately, the providing may be performed by a lens distributor that arranges for the delivery of the ophthalmic lenses to the lens wearer.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present invention will now be described by way of example only with reference to the accompanying schematic drawings of which.

DETAILED DESCRIPTION

Figure 1:
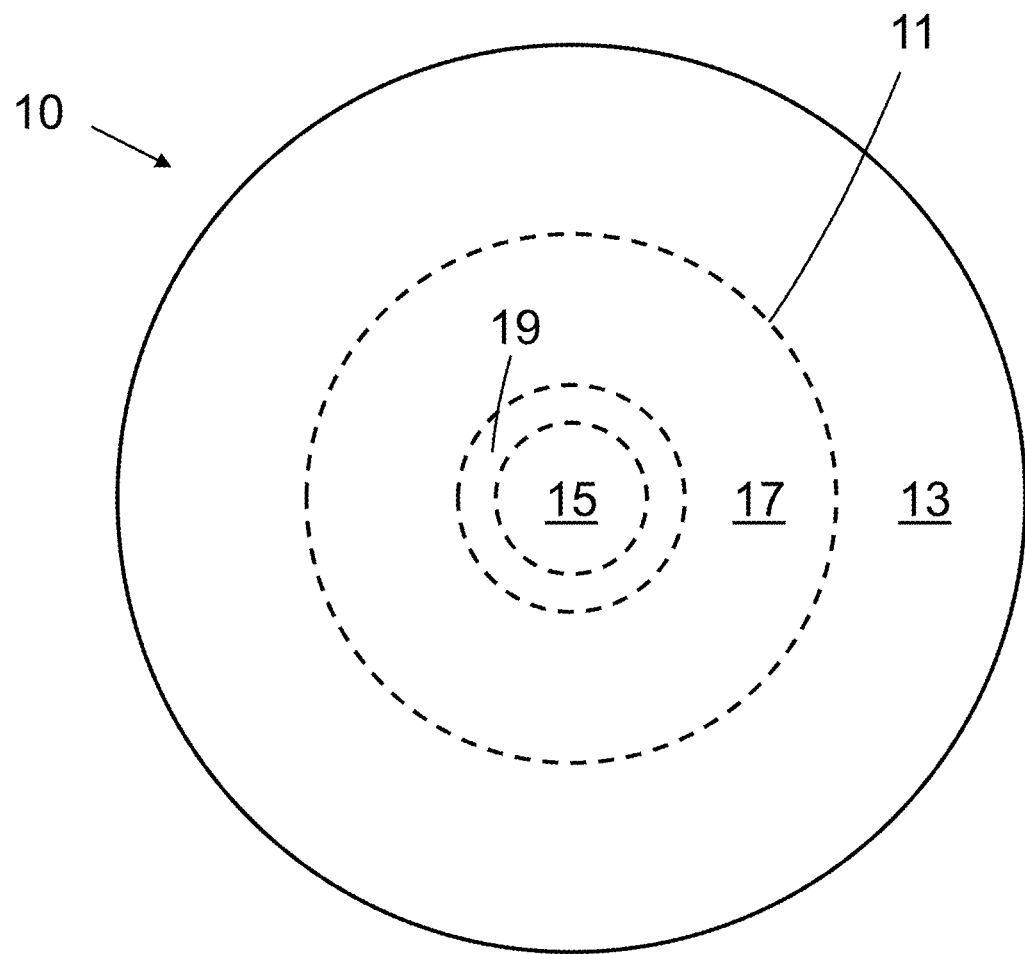
FIG. 1 shows a contact lens according to example embodiments of the invention.

The present invention provides, according to the first aspect, an ophthalmic lens for myopia control. A first surface of the ophthalmic lens varies to form a first surface power map. A second surface of the ophthalmic lens varies to form a second surface power map. It will be appreciated by the skilled person that the variation of a surface comprises a variation in the curvature of the surface. The first and second surface power maps each comprise a spiral. The spirals provided by the first and second surface power maps twist in opposing directions.

The spirals formed on each of the first and second surfaces may be formed by varying the power of the respective surface substantially periodically both radially outwards from and angularly about an optical axis of the lens.

It will be appreciated by the skilled person that the first surface power map need not necessarily be formed of the entirety of the first surface. In fact, the first surface power map may be formed on a portion of the first surface. In such a case, variation of the first surface outside of the portion is not relevant to the first surface power map. The same applies to the second surface and the second surface power map. For example, in the case of a contact lens, the surface power maps may be formed by only an optic zone of the contact lens, and not by a surrounding peripheral zone. Thus, in that case, the portion of the surfaces corresponds to the optic zone of the contact lens.

An ophthalmic lens providing first and second surfaces having counter-rotating spirals can provide a lens power profile which is effective in a myopia control context. It is believed that myopic defocus can influence eye growth. However, whilst it is established that myopia control lenses are effective in inhibiting myopia progression, the mechanism by which they achieve this effect is not yet fully known or understood. The effectiveness of the structures and lens designs presently disclosed for use in myopia control is not reliant on the correctness of the above theories on the precise mechanism by which myopia control lenses work.

It may be that the ophthalmic lens is a contact lens. Alternatively, the ophthalmic lens may be an intraocular lens or a spectacle lens.

It will be appreciated that the variations of the first surface power map need not necessarily match those of the second surface power map. Indeed, the first surface power map vary independently of the second surface power map, and vice versa. Thus, each of the subsequently described optional features of the characteristics of the radial and angular variations apply to the first and second surface power maps together or separately.

It may be that the spirals are formed on a portion of the lens. For example, in the case of a contact lens, the spirals may be formed in an optic zone of the lens.

In the case of contact lenses, it will be appreciated that the lens will comprise an optic zone, which may provide vision modification. Contact lenses according to embodiments of the invention may also comprise a surrounding peripheral zone, which provides no additional focussing or vision modification. The peripheral zone may serve merely to help maintain the contact lens in position on the wearer's eye. Thus, it will be appreciated by the skilled person that the surface power map is defined by the variation of the first surface across the optic zone of the lens. Variation of the lens surface outside of the optic zone (for example, in a peripheral zone) is not, in the context of the present invention, to be treated as defining the surface power map. Similar considerations also apply to intraocular lenses, which may also comprise an optic zone and (optionally) a peripheral zone.

It may be that the optic zone of a contact lens according to embodiments of the present invention has a diameter of between 4 mm and 9 mm, depending on the type of contact lens. For example, the diameter of the optic zone may be about 5 mm, or about 6 mm, or about 7 mm, or about 8 mm. The diameter of the optic zone of the contact lens may be between 7 mm and 9 mm. The optic zone includes an optical axis that corresponds to the geometric centre of the optic zone.

A period of the radial variations (for example the radial variations of both the first and second surface power maps) may be greater than 100 microns. A period of the angular variations (for example the radial variations of the both the first and second surface power maps) may be greater than 6 degrees.

It may be that, for the first and/or the second surface power maps, one or both of the radial and angular variations are of constant magnitude across the power map.

It may be that a period of the radial variations is greater than 200 microns, preferably greater than 400 microns, and more preferably greater than 800 microns. It may be that a period of the angular variations is greater than 6 degrees, preferably greater than 9 degrees, preferably greater than 18 degrees, and more preferably greater than 36 degrees. The periods of the radial variations may be between 0.1 mm and 10 mm. The periods of the radial variations may be between 0.5 mm and 5 mm. The periods of the radial variations may be between 1 mm and 2 mm.

The periods of the angular variations may be less than 180 degrees, preferably less than 90 degrees, more preferably less than 45 degrees. The periods of the angular variations may be between 180 degrees and 9 degrees. The periods of the angular variations may be between 120 degrees and 24 degrees. The periods of the angular variations may be between 90 degrees and 36 degrees. The spirals may each comprise more than two, preferably more than 4, more preferably more than 8 arms. It will be appreciated by a person skilled in the art that the period of the angular sinusoidal variation determines the number of arms on a spiral. Thus, it may be that the radial variation has a period of greater than 100 microns and the angular variation has a period of greater than 6 degrees, preferably greater than 9 degrees, more preferably greater than 18 degrees, and yet more preferably greater than 36 degrees. It may be that the radial variation has a period of greater than 200 microns and the angular variation has a period of greater than 6 degrees, preferably greater than 9 degrees, more preferably greater than 18 degrees, and yet more preferably greater than 36 degrees. It may be that the radial variation has a period of greater than 400 microns and the angular variation has a period of greater than 6 degrees, preferably greater than 9 degrees, more preferably greater than 18 degrees, and yet more preferably greater than 36 degrees. It may be that the radial variation has a period of greater than 800 microns and the angular variation has a period of greater than 6 degrees, preferably greater than 9 degrees, more preferably greater than 18 degrees, and yet more preferably greater than 36 degrees. It will be appreciated that the above applies to either the surface of the lens.

It may be that the spirals formed on the first and second surface power maps twist in opposing directions but are otherwise substantially identical.

It may be that the power varies smoothly across the power maps. It may be that power varies continuously, without any discontinuities. It may be that the power varies across the portion at a rate of less than 80 D/mm, preferably less than 40 D/mm, more preferably less than 20 D/mm. It may be that the surface varies smoothly across the portion. It may be that surface varies continuously, without any discontinuities. Varying the power smoothly across the power maps can result in a lens surface profile which is easier to manufacture using a lathe. It will be appreciated by the skilled person that manufacturing an ophthalmic lens using a lathe may comprise using a lathe to shape a surface of one or more of a lens (for example a contact lens), a mould for a lens (for example a mould for a contact lens), and an insert for a lens mould (for example an insert for a contact lens mould). Sharp transitions and features can be difficult to achieve using a lathe. Therefore, lenses having such features are often not reproducible with the intended or required definition when manufactured using a lathe. Thus, it will also be appreciated that the term smoothly in this context means smooth enough to enable the desired shaping of the surface of a lens, a mould for a lens, or an insert for a lens mould using a lathe.

The power maps may vary as a square wave in one or both of the radial and angular directions. The power maps may vary as a rounded square wave in one or both of the radial and angular directions. The power maps may vary as a sinusoid in one or both of the radial and angular directions.

It may be that the radial and angular variations are associated with a respective waveform. In addition, a power distribution of the waveforms may be symmetrical with a substantially equal balance between myopic defocus and distance vision correction. Alternately, the power distribution may be biased towards either vision correction or myopic defocus. Thus, the power distributions of the waveforms may be asymmetric in one or both of the radial direction and the angular direction.

The periods of one or both of the radial and angular variations may be substantially constant across the power maps. Embodiments of the invention in which the radial and angular variations are substantially constant yield a lens with surface profiles which are easier to manufacture using a lathe.

The periods of one or both of the radial and angular variations may change according to either or both of a radial distance from the optical axis of the lens and an angular position about the optical axis. Embodiments of the invention in which the period of one or both of the radial and angular variations change according to position on the lens can provide a lens in which the characteristics of the spiral (for example its rate of rotation or arm width) differ in different regions of the optic zone. It will be appreciated that the optical axis of a contact lens is also generally the centre of the optic zone of the contact lens.

Changes in the periods of the radial variations may be separated by a blending region, for example of linearly varying lens power. Such a blending region may comprise a concentric ring of linearly varying period between a first region having a first period of radial variation and a second region having a second period of radial variation. Thus, the blending region may provide a smooth transition between regions of different period radial variation. It may be that regions of different period radial variation are separated by two blending regions and an intervening region of substantially constant lens power. The blending region may have a width (in plan view) of from about 25 micrometers to about 200 micrometers.

It may be that each arm of one or both of the spirals twists through between a quarter of a rotation and 40 rotations. It will be appreciated by a person skilled in the art that the number of rotations that an arm of a spiral twists through is determined by the period of the radial variation and the radius of the surface power map.

It may be that a ratio of the period of the radial variation to that of the angular variation is greater than 0.1 mm:6°. It may be that each arm of one or both of the spirals is wider than 0.1 mm, preferably wider than 0.5 mm, more preferably wider than 1 mm. It may be that each are is between 0.1 mm and 3 mm wide. It may be that each arm is between 0.25 mm and 2 mm wide. It may be that each arm is between 0.5 mm and 1 mm wide. It will be understood by a person skilled in the art that a width of an arm at a given radius is defined as its perpendicular width (i.e. its width in the direction perpendicular to the given radius). The width of the arm is, in this context, defined as the distance between two points immediately adjacent each side of the arm, both points having either a maximum or a minimum gradient, between which the power undergoes a single positive or negative excursion. The skilled person will appreciate that such a definition of width provides a straight line measurement of arm width along a tangent to a circle of the given radius. The skilled person will further appreciate that a measurement of width under this definition will differ from a measurement of the width of an arm taken as an arc of a circle having the given radius. Unlike a width measurement under the straight-line width definition, such an arc-based measurement would be proportional to the angular period. The magnitude of the difference between the widths obtained by these two methods will depend on the angular period in the particular case at hand.

It may be that each of the spirals comprises more than 2 arms, preferably more than 4 arms, more preferably more than 8 arms, and yet more preferably more than 16 arms.

It may be that each of the arms of the spiral twists through at least half a rotation, preferably at least a whole rotation, more preferably at least one and a half rotations, and yet more preferably at least two rotations.

It may be that each arm of the spirals extends from the optical axis of the portion to the periphery of the power map. Contact lenses according to embodiments of the invention in which the arms of the spirals extend from the optical axis of the lens to the periphery of the power maps can provide a substantially constant ratio of the first lens power (corresponding to distance vision focussing) to the second lens power (corresponding to myopic defocus) in the presence of varying pupil dilation. Such embodiments may provide a more consistent myopic defocussed image in varying light conditions compared to concentric ring lens designs. If the ophthalmic lens is a contact lens, the myopic defocussed image can be more consistent upon lens decentration compared to concentric ring contact lens designs. If the ophthalmic lens is a spectacle lens, the myopic defocussed image can be more consistent upon eyeball rotation compared to other spectacle lens designs.

It will be appreciated that the lens will have a means lens power. Furthermore, it will be appreciated that the lens will be divided between a first area of the lens having a lens power greater than the mean and a second area of the lens having a lens power less than the mean. It may be that a ratio of the first area to the second area is between 10:1 and 1:10. It may be that a ratio of the first area to the second area is between 5:1 and 1:5. It may be that a ratio of the first area to the second area is between 3:1 and 1:3. It may be that a ratio of the first area to the second area is between 2:1 and 1:2. It may be that a ratio of the first area to the second area is approximately 1:1.

The power maps may comprise a central region and an outer region. The central region may immediately surround the optical axis of the lens. The outer region may immediately surround the central region. It may be that the power of the central region does not vary periodically across the central region. The outer region may comprise the spiral power profile. Thus, the outer region may comprise the angular and radial variations in power of the first and/or second surface power maps. It may be that the spirals are formed in the central region. In such cases, it may be that the spirals do not extend into the outer region. Alternatively, the spirals may be formed in the outer region. In such cases, it may be that the spirals do not extend into the central region. Alternatively, it may be that the central region comprises the spiral power profile and the outer region does not vary periodically (for example, being substantially constant) across the outer region. It may be that the non-varying region of the lens provides vision correction, for example by comprising a power for myopia correction (i.e. to provide clear distance vision). Alternatively, it may be that the non-varying region of the lens does not provide any vision modification, and thus simply provides part of the lens through which normally focussed vision is possible. Providing a contact lens in which a central or outer region has a lens power free from periodic power variation can allow the lens to provide simultaneous myopia control and correction.

Thus, it may be that one or more portions of the lens are arranged to provide functions other than myopia control. For example, it may be that the central region of the lens has a lens power chosen to provide vision correction, for example myopia correction. It will be appreciated that such a region of the lens can be arranged to provide any vision correction of the types achievable in known contact lenses and spectacle lenses. Thus, it may be that the spirals formed by the first and second surface power maps are present only in one or more specific myopia control portions of the lens. Such portions of the lens may take any shape, for example annular rings, strips projecting radially outwards from the centre of the lens, or one or more of the alternating portions of the pseudo-dartboard pattern. It may be that the spiral power profiles formed by the first and second surface power maps are interrupted at a predetermined radial distance from the optical axis of the lens by an annular ring shaped portion of corrective lens power. It may be that the lens comprises multiple such corrective ring portions. It may be that the spiral power profile continues between the corrective ring portions.

A contact lens according to an embodiment of the invention may include a surrounding peripheral zone, which provides no additional focussing or vision correction and serves merely to help maintain the contact lens in position on the wearer's eye.

When worn on an eye, the contact lens rests on the cornea and the optic zone approximately covers the pupil of the wearer, in the conventional manner. Thus, the diameter of the central region may be less than 50%, preferably less than 40%, more preferably less than 30%, of that of the power map. The central region may be smaller than the minimum pupil size of a wearer of the contact lens. Such embodiments of the invention can provide a central region which is smaller than the minimum pupil size of the wearer. Embodiments of the invention having a central region which is smaller than the minimum pupil size of the wearer can maintain vision correction in the presence of varying light conditions.

The lens may comprise a transition region. The transition region may surround the central region. The outer region may surround the transition region. It may be that the power of the transition region varies to provide a smooth transition between the central and outer regions. Embodiments of the invention providing a smooth transition between the central and outer regions can enable easier manufacture using a lathe of a lens, a mould for such a lens, or an insert for such a lens mould. Thus, it will be appreciated by the skilled person that smooth in this context means that the lens profile must be smooth enough to be produced using a lathe. It may be that the transition region also varies as a spiral, for example a continuation of the spiral formed in the outer region. In such embodiments, a magnitude of the spiral formed in the transition region may decay (for example, linearly) between an outermost radius of the transition region and an innermost radius of the transition region. It may be that the transition spiral decays from a magnitude equal to that of the spiral formed in the outer region (for example, at the outermost radius) to zero (for example, at the innermost radius).

The periods and phases of the radial and angular variations of the second surface power map may be the same as those of the first surface power map. Thus, the spirals provided by the first and second surface power maps may be the same but for the opposing twist directions. Providing first and second surface power maps comprising counter-rotating spirals can give a lens power map which approximates a dartboard-like pattern of alternating annular rings. It will be appreciated by a person skilled in the art that the lens power map is formed by the superposition of the power maps of each of the first and second surfaces. Thus, it will also be appreciated that the pseudo-dartboard pattern is provided by the combination of the first and second surface power maps, each of which retains the previously described benefits of ease of manufacture. Thus, such embodiments can enable easier manufacture of a lens having a pseudo-dartboard power map using a lathe.

The lens power map may comprise a plurality of sections. The plurality of sections may provide either a first power corresponding to a desired vision correction or a second power corresponding to a desired myopic defocus. Accordingly, the first power may be between 0 diopters (D) and −10 D. The first power may be from −0.25 D to −6.00 D. The second power provided in the present lenses may be more positive than the first power of the lens, for example, the second power may be from 1 D to 5 D more positive than the first power. The second power may be 1 D to 4 D more positive than the first power. The second power may be 2 D to 3 D more positive than the first power. The second power may vary, such as may occur when providing discrete segments of defocus with more positive power than the first power, such that some of the segments may have a second power of +1 D, some segments may have a second power of +2 D, and some segments may have a second power of +3 D. The variation of the second power may occur within the same arm, or may occur in different arms. The sections may arranged on the lens such that they alternate radially and/or angularly between the first power and the second power.

A contact lens according to an embodiment of the invention may comprise a ballast to orient the lens when positioned on the eye of a wearer. It may be that the contact lens provides particular benefit to the wearer in a given orientation. Embodiments of the invention incorporating a ballast into the contact lens will, when placed on the eye of a wearer, rotate under the action of the wearer's eyelid to a pre-determined angle of repose; for example the ballast may be a wedge and the rotation may result from the action of the eyelid on the wedge. By positioning the ballast in the contact lens, it is possible to ensure that the angle of repose corresponds to a lens orientation providing particular benefit to the wearer.

The present invention provides, according to the second aspect, a method of manufacturing an ophthalmic lens (for example a contact lens) for myopia control. The method comprises operating a lathe to shape first and second surfaces of one of: a lens (for example a contact lens), a mould for a lens (for example a mould for a contact lens), or an insert for manufacturing a mould for a lens (for example an insert for a mould for a contact lens). The first surface forms a first surface power map. The second surface forms a second surface power map. Each of the first and second surface power maps comprise a spiral. The spirals formed by the first and second surface power maps twist in opposing directions.

It may be that each of the spirals are formed by varying a power of the respective surface substantially periodically both radially outwards from and angularly about an optical axis of the lens.

It may be that the method comprises operating a lathe to shape the surface of a lens. Alternatively or additionally, the method may comprise operating a lathe to shape the surface of a mould for a lens. Alternatively or additionally, the method may comprise operating a lathe to shape the surface of an insert for manufacturing of a mould for a lens. It will be appreciated by the skilled person that the further removed the subject of the shaping by the lathe is from the lens, the less feature definition that will reproduced on the resulting lens. Thus, for example, shaping the surface of a lens using a lathe enables more defined surface features than will be achievable when using the lathe to shape the surface of a mould for a lens.

In embodiments of the invention in which the lens is a contact lens or an intraocular lens, the first and second surface power maps may be formed by shaping an optic zone of the first and second surfaces. It will be appreciated that an optic zone of a mould or an insert for a mould refers to the part of the mould which corresponds to the optic zone of a contact lens manufactured using that mould or insert.

Lenses, for example contact lenses, according to the present invention can be formed by cast moulding processes, spin cast moulding processes, or lathing processes, or a combination thereof. As understood by persons skilled in the art, cast moulding refers to the moulding of a lens member by placing a lens forming material between a female mould member having a concave lens member forming surface, and a male mould member having a convex lens member forming surface.

In embodiments in which the ophthalmic lens comprises a contact lens, the contact lens material, as it is used as a portion of a contact lens or as an entire contact lens, is visually transparent (although it can include a handling tint). The contact lens material can be a hydrogel material, a silicone hydrogel material, or a silicone elastomer material, as understood in the art. In other words, the present contact lens can comprise, consist essentially of, or consist of a hydrogel material, a silicone hydrogel material, or a silicone elastomer material. As understood in the field of contact lenses, a hydrogel is a material that retains water in an equilibrium state and is free of a silicone-containing chemical. A silicone hydrogel is a hydrogel that includes a silicone-containing chemical. Hydrogel materials and silicone hydrogel materials, as used herein, have an equilibrium water content (EWC) of at least 10% to about 90% (wt/wt). The hydrogel material or silicone hydrogel material may have an EWC from about 30% to about 70% (wt/wt). In comparison, a silicone elastomer material, as used herein, has a water content from about 0% to less than 10% (wt/wt). Typically, the silicone elastomer materials used with the present methods or apparatus have a water content from 0.1% to 3% (wt/wt). Alternatively, examples of the present contact lenses can be made from rigid gas permeable materials, such as polymethyl methacrylate (PMMA) and the like.

The present methods may include a step of forming a contact lens in a moulding assembly, which comprises a first mould part and a second mould part assembled together. In the case of hydrogel lenses or silicone hydrogel lenses, the lenses can be made by polymerizing a hydrogel or silicone hydrogel lens formulation that includes a polymerization initiator in a lens shaped cavity formed between the first mould part and the second mould part. For silicone elastomer lenses, the lenses can be made by curing, vulcanizing, or catalysing, such as by hydrosylation, a liquid silicone elastomer material in a lens shaped cavity formed between the first mould part and the second mould part. The surface of each mould part that forms the contact lens shaped cavity may be convex, concave, planar or a combination of thereof. After formation of the contact lens, the two mould parts are separated such that the contact lens remains attached to the surface of one of the mould parts. As a result, a contact lens is provided on a surface of the first or second mould part. It may be desirable to place the lens member on a surface of a mould part that was not used to produce the first lens member, but that may require additional steps to achieve the desired alignment of the member to the mould part. The lenses may then be removed from the mould part to which they are attached, and further processed, such as by extraction and hydration, and inspected, and packaged in a package and sterilized.

FIG. 1 shows a contact lens 10 according to embodiments of the invention. The contact lens 10 comprises an optic zone 11 and a peripheral zone 13. The optic zone 11 comprises the part of the lens through which a wearer of the contact lens sees. The optic zone 11 forms a lens designed to provide vision correction to the wearer. The peripheral zone 13 surrounds the optic zone 11 and does not provide any vision correction to the wearer. The peripheral zone 13 may perform other functions. For example, the peripheral zone 13 may serve to help maintain the contact lens on the wearer's eye. The peripheral zone 13 may include a ballast in order to maintain a predetermined orientation of the contact lens on the wearer's eye.

The two surfaces of the contact lens are shaped such that they vary across the optic zone 11 to form first and second surface power maps. The first and second surface power maps together form a lens power map. Thus, the optic zone can be said to provide a first surface power map, a second surface power map, and a lens power map. Within the optic zone the power maps may comprise one or more distinct regions. The example contact lens shown in FIG. 1 comprises a central region 15, an outer region 17, and a transition region 19. The outer region 17 surrounds the transition region 19. The transition region 19 surrounds the central region 15. The central region 15 and the outer region 17 may provide differing arrangements of lens power, such that they provide different vision corrections. The transition region 19 may serve for provide a smooth transition between the central region 15 and the outer region 17. It will be appreciated that the contact lens illustrated in FIG. 1 is provided merely as an example and that other contact lenses according to the invention may include more or fewer regions. For example, contact lenses according to embodiments of the invention may omit the transition region, or may even comprise only a single region across the whole of optic zone 11. Contact lenses according to embodiments of the invention may include additional regions, for example formed as concentric circles.

According to a first example embodiment of the invention, there is provided a contact lens for myopia control. It will be appreciated that alternative embodiments may comprise an intraocular lens or a spectacle lens. The contact lens comprises a first surface and a second surface. In this example embodiment, the first surface comprises an outer surface of the contact lens and the second surface comprises an inner surface of the contact lens. It will be appreciated by the person skilled in the art that the outer surface is the convex surface of the contact lens adjacent to a wearer's eyelid and that the inner surface is the concave surface of the contact lens adjacent the wearer's eye.

The first surface is shaped to form a first surface power map. In this example embodiment, the first surface power map is formed by only a portion of the first surface. The portion of the first surface, in this case, is defined by and corresponds to an optic zone of the contact lens. Thus, the first surface power map can also be said to be provided by variation of a first surface of the optic zone.

The optic zone of the contact lens provides any vision modification by the lens. A contact lens according to embodiments of the invention may also comprise a surrounding peripheral zone, which provides no additional focussing or vision modification. In the case of such a contact lens, the peripheral zone may serve merely to help maintain the contact lens in position on the wearer's eye. Thus, it will be appreciated by the skilled person that, in such embodiments, the first surface power map is defined by the variation of the first surface across the optic zone of the lens. Similarly, the second surface power map is defined by variation of the second surface across the optic zone. Variation of the lens surfaces outside of the optic zone (for example, in a peripheral zone) does not, in these embodiments, affect the surface power maps.

It will be appreciated by the skilled person that the first surface power map shows the modification to the overall contact lens power map provided by the shape of that surface. Thus, a contact lens having two surfaces (an inner surface and an outer surface) will comprise two surface power maps, the combination of which determines the overall contact lens power map.

Figure 2:
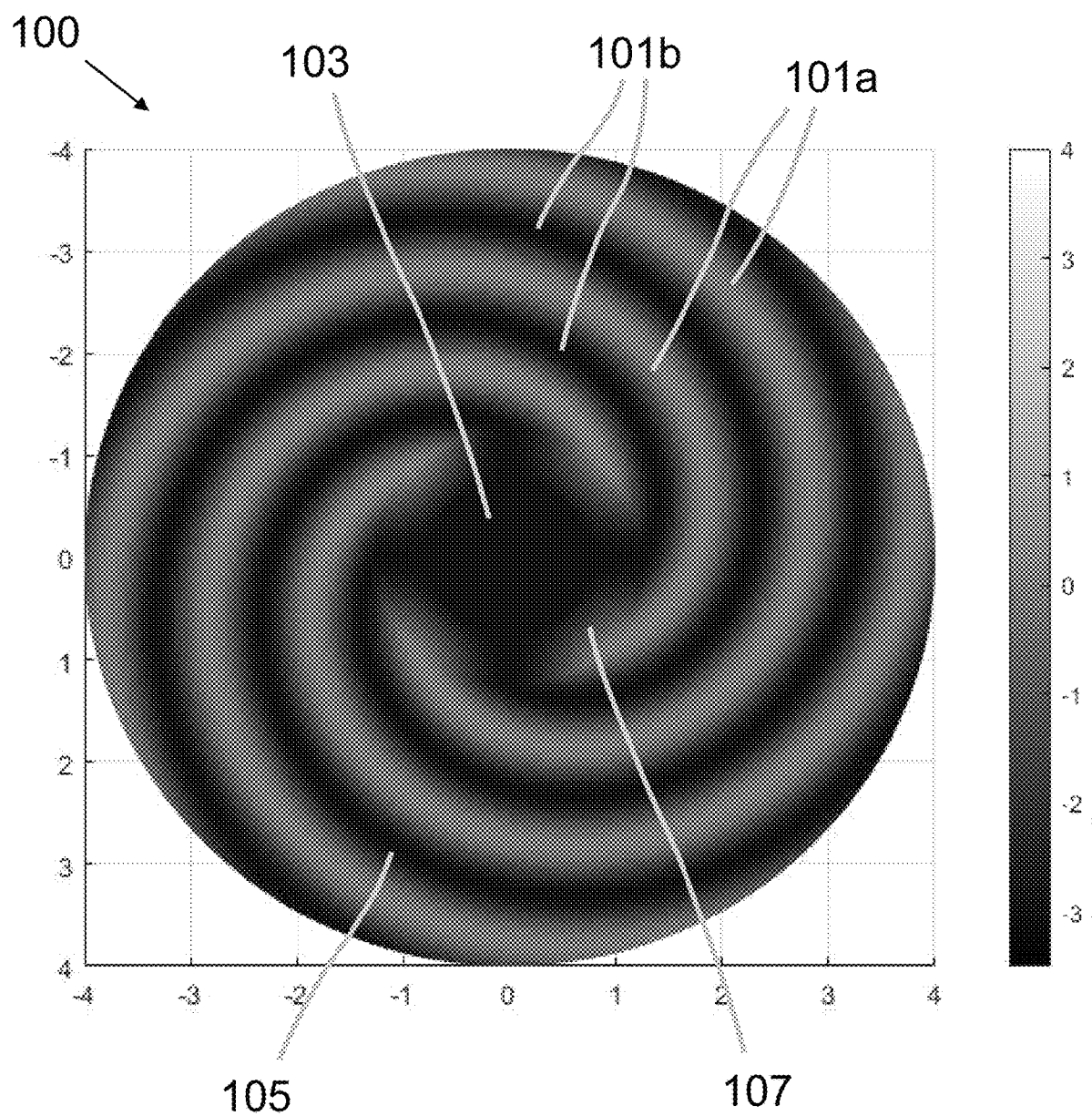
FIG. 2 shows a first surface power map of an optic zone of a contact lens according to a first embodiment of the invention.

FIG. 2 shows the first surface power map 100. The first surface power map 100 forms a spiral. The spiral comprises a plurality of (in this example 4) arms 101. Each of the arms 101 comprises one of a peak arm 101a and a trough arm 101b. It will be appreciated that a peak arm 101a is an arm which constitutes a positive excursion from the mean power of the surface power map (or the periodically varying region of the surface power map), and that a trough arm 101b is an arm which constitutes a negative excursion from the mean power of the surface power map (or the periodically varying region of the surface power map). The spiral is formed by varying the power substantially periodically both radially outwards from and angularly about an optical axis of the contact lens. It will be appreciated that an optical axis of a contact lens is equivalent to an optical axis of the optic zone of that contact lens. The power varies between a first lens power and a second lens power. The first surface power map of this example embodiment has a base lens power of −3.0 D with an add power of +3.0 D. Thus, the first lens power is −3.0 D and the second lens power is +0 D. It will be appreciated by a person skilled in the art that the specific values of the first lens power and the second lens power (and therefore the base lens power and add power) provided are purely examples, and that the actual values used in a given situation will be determined by the needs of the intended wearer.

In this example embodiment, the period of the radial variation is 1.2 mm and the period of the angular variation is 90 degrees. However, it will be appreciated that, in alternative embodiments, other periods of the radial and/or angular variation may be used. The period of the radial variation need only be greater than 100 microns and the period of the angular variation need only be greater than 6 degrees.

In this particular embodiment, the power varies smoothly across the first surface power map 100, substantially as a sinusoid in both the radial and angular directions. Having the surface power map vary smoothly across the first surface power map provides for easier manufacture using a lathe of the contact lens or of apparatus (for example, a mould or an insert for a mould) for manufacturing the contact lens. However, in alternative embodiments, the power may vary according to other waveforms. For example, the power may vary as a square wave or as a rounded square wave in one or both of the radial and angular directions. Thus, in alternative embodiments, the power need not necessarily vary smoothly across the first surface power map.

In this example embodiment, the positive and negative excursions of the sinusoid are of equal length, such that the sinusoid can be said to have a 50% duty cycle. Alternative embodiments comprise variations having other duty cycles. Thus, in such embodiments, the positive excursion may be of a different length than the negative excursion.

It will be appreciated that, the width of the arms 101 of the spiral is determined at least in part by the ratio of the period of the radial variation to that of the angular variation. In this example embodiment, each arm 101 of the spiral is approximately 500 microns wide. It will be appreciated that alternative embodiments may incorporate arms 101 having different widths. It will also be appreciated that the width of an arm 101 is defined as its perpendicular width.

Similarly, in this example embodiment, the periods of the radial and angular variations are each substantially constant across the first surface power map. However, in alternative embodiments, the period of at least one of the radial and angular variations may change according to one or both of a radial distance from the optical axis of the lens and an angular position about the optical axis of the lens.

In alternative embodiments, the period of the angular variation is less than 180°. It will be appreciated by a person skilled in the art that the period of the angular variation determines the number of arms 101 on the spiral. Thus, in such embodiments, the spiral comprises at least two arms. It will therefore also be appreciated that certain values of angular variation, specifically those which are unit fractions of 360 degrees, may be particularly advantageous in that they allow for a surface power profile without angular discontinuities.

In this example embodiment, each arm 101 of the spiral twists through an angle of 270 degrees (or 0.75 of a rotation). In alternative embodiments of the invention, each arm 101 of the spiral may twist through between a quarter of a rotation (90 degrees) and 40 rotations.

In this particular embodiment, the first surface power map 100 comprises a central region 103 and an outer region 105. The central region 103 immediately surrounds the optical axis of the contact lens. The outer region 105 surrounds the central region 103. The power of the central region does not vary periodically across the central region 103 and may, for example, be substantially constant across the central region 103. The outer region 105 comprises the spiral power profile and, therefore, the angular and radial variations in power.

In alternative embodiments of the invention, the central region comprises the spiral power profile and the outer region does not vary periodically across the outer region (for example, the outer region may have a substantially constant lens power). In other alternative embodiments of the invention, each arm 101 of the spiral extends from the centre of the first surface power map to the periphery of the first surface power map. Thus, such embodiments do not comprise distinct central and outer regions.

In this example embodiment, the central region 103 has a diameter of 2 mm, which corresponds to 25% of the 8 mm diameter of the power map. In this example embodiment, the power map corresponds to the optic zone of the contact lens. Thus, the optic zone, through which the wearer sees, provides the first surface power map 100 shown in FIG. 2. The contact lens may in addition comprise a surrounding peripheral zone, which provides no additional focussing or vision modification and serves merely to help maintain the contact lens in position on the wearer's eye. In other embodiments, the diameter of the central region may be less than 25% of that of the power map (or optic zone). However, it will be appreciated that, in alternative embodiments of the invention, the diameter of the central region 103 may take other values. Similarly, it will be appreciated that the ratio of the diameter of the central region 103 to that of the power map may also take other values. For example, the diameter of the central region 103 may be less than 30% of that of the power map (or optic zone).

In embodiments, the central region 103 may be smaller than the minimum pupil size of a wearer of the contact lens. Such embodiments maintain effective myopia control even when the wearer's pupil constricts to its minimum size. If the central region 103 is larger than the minimum pupil size, when the wearer's pupil constricts to its minimum size, only the central region 103 will be positioned across the wearer's entrance pupil. As the power of the central region 103 does not vary as a spiral across the central region 103, it may be that the lens does not provide effective myopia control for any pupil sizes smaller than the central region 103. It will be appreciated that, in spectacles according to embodiments of the present invention, the wearer's eye may move independently of the lens. Therefore, such lenses may nonetheless provide effective myopia control when the central region is smaller than the wearer's minimum pupil size.

This example embodiment further comprises a transition region 107. The transition region 107 surrounds the central region 103. The outer region 105 surrounds the transition region 107. The power of the transition region 107 varies to provide a smooth transition between the central region 103 and the outer region 105. It will be appreciated that such a transition region 107 is not essential and therefore that alternative embodiments do not include a transition region 107. It will be appreciated that smooth, in this context, is defined as being smooth enough for the corresponding lens curvature to be reproduced by a lathe. In this example embodiment, the transition region is approximately 300 microns wide. It will, however, be appreciated that other widths of transition region may also be used.

Figure 3:
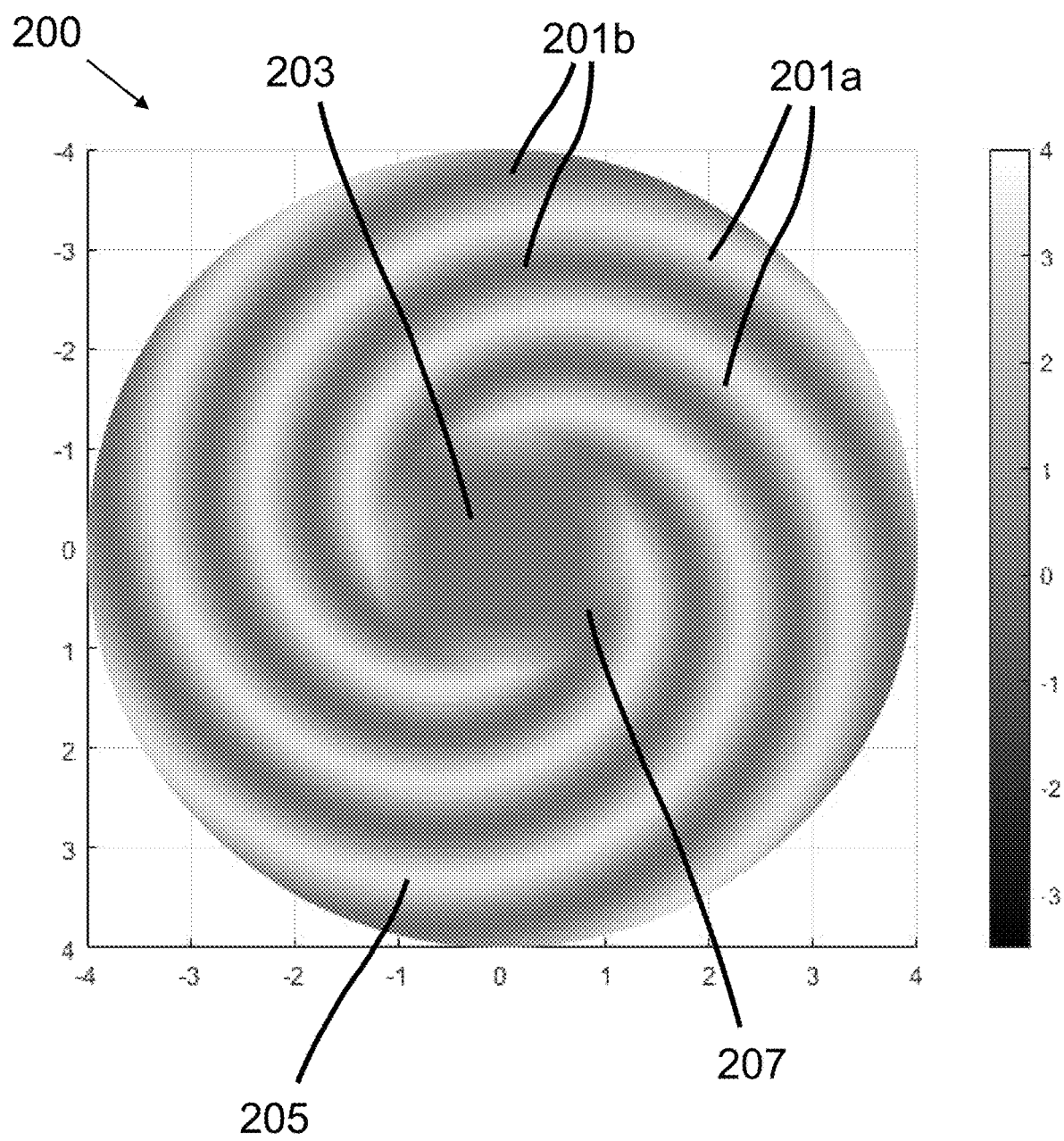
FIG. 3 shows a second surface power map of the optic zone of the contact lens of the first embodiment.

It will be appreciated by the skilled person that the second surface of the contact lens forms a second surface power map. The second surface power map is also provided by only a portion of the second surface, that portion also corresponding to the optic zone of the contact lens. The second surface power map 200 (FIG. 3) also varies substantially periodically both angularly about and radially outwards from the optical axis of the lens. Thus, the second surface power map 200 also comprises a spiral. As in the case of the first surface, the spiral comprises a plurality of arms 201, including peak arms 201a and trough arms 201b. In this example embodiment, the periods of the radial and angular variations of the second surface power map 200 are the same as those of the first surface power map 100. However, a skilled person will appreciate that alternative embodiments may incorporate variations having different periods on the second surface power map 200 to one or both of those of the first surface power map 100. The period of the angular variation of the second surface power map 200 may be greater than 6 degrees. Similarly, in alternative embodiments the period of the radial variation of the second surface power map 200 may be greater than 100 microns. In this example embodiment, the second surface power map 200 also comprises a central region 203, an outer region 205, and a transition region 207.

Figure 4:
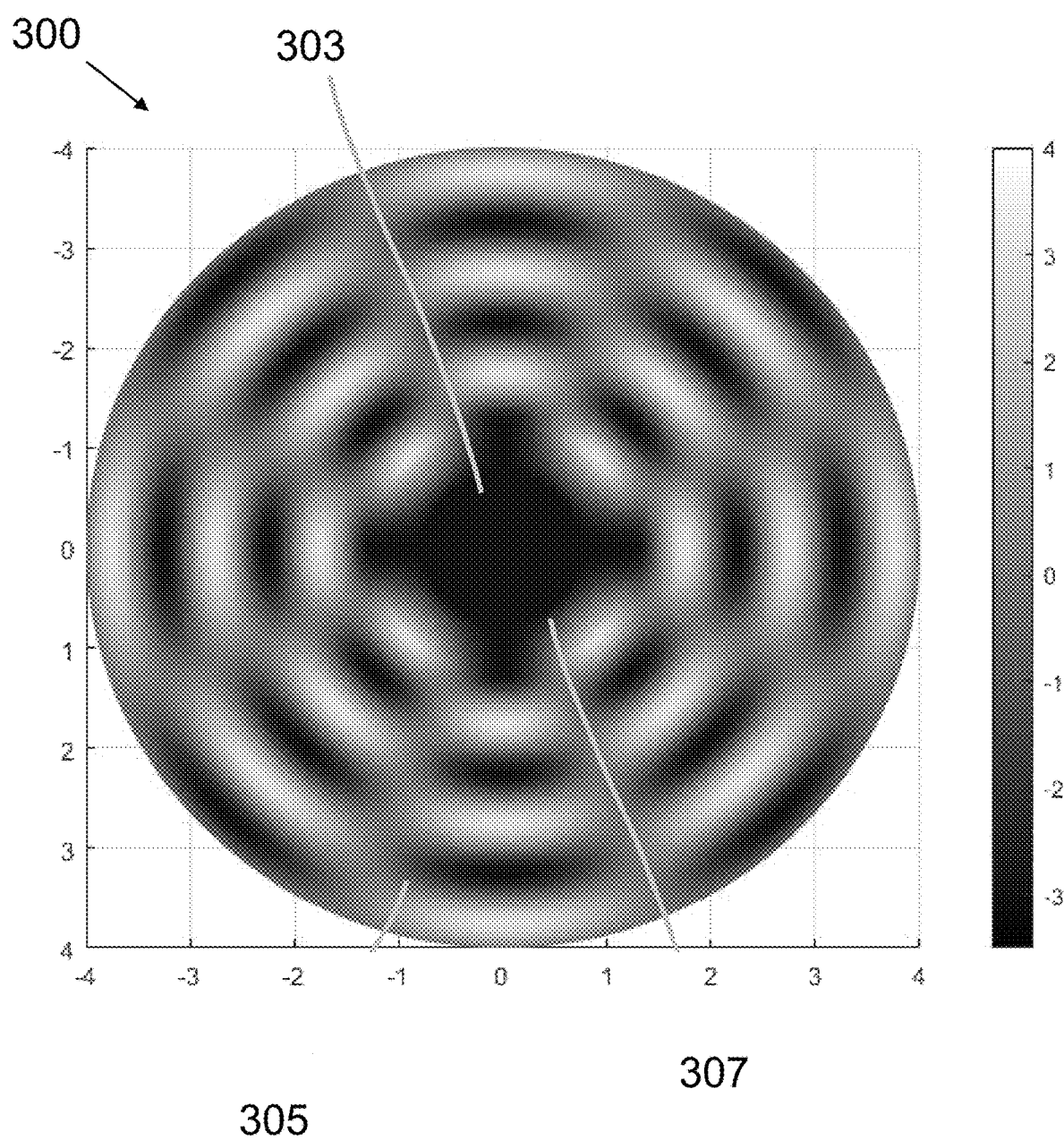
FIG. 4 shows a lens power map of the optic zone of the contact lens of the first embodiment.

The spiral formed by the second surface power map 200 twists in the opposite direction to that formed by the first surface power map 100. Thus, in this particular embodiment, the spirals provided by the first surface power map 100 and the second surface power map 200 are the same but for the opposing twist directions. The power map of the contact lens is determined by the superposition of the power maps of the first surface power map 100 and the second surface power map 200. FIG. 4 shows an overall lens power map of the contact lens of the first embodiment.

The superposition of the two counter-rotating spirals formed by the first surface power map 100 and the second surface power map 200 results in a lens power map which approximates a pseudo-dartboard pattern of annular rings of alternating segments. The lens power approximately alternates between a first lens power and a second lens power in both the radial and angular directions. Because the power alternates between the first lens power and the second lens power angularly, the contact lens also provides a monotonic change in the ratio of the first lens power to the second lens power as a wearer's pupil constricts. Thus, the contact lens 300 also provides a more constant ratio of lens powers providing myopic defocus to those providing distance vision focussing in variable light conditions.

As both the first surface power map 100 and the second surface power map 200 comprise central, peripheral, and transition regions, the overall power map of the contact lens 300 also comprises a central region 303, an outer region 305, and a transition region 307.

Figure 5:
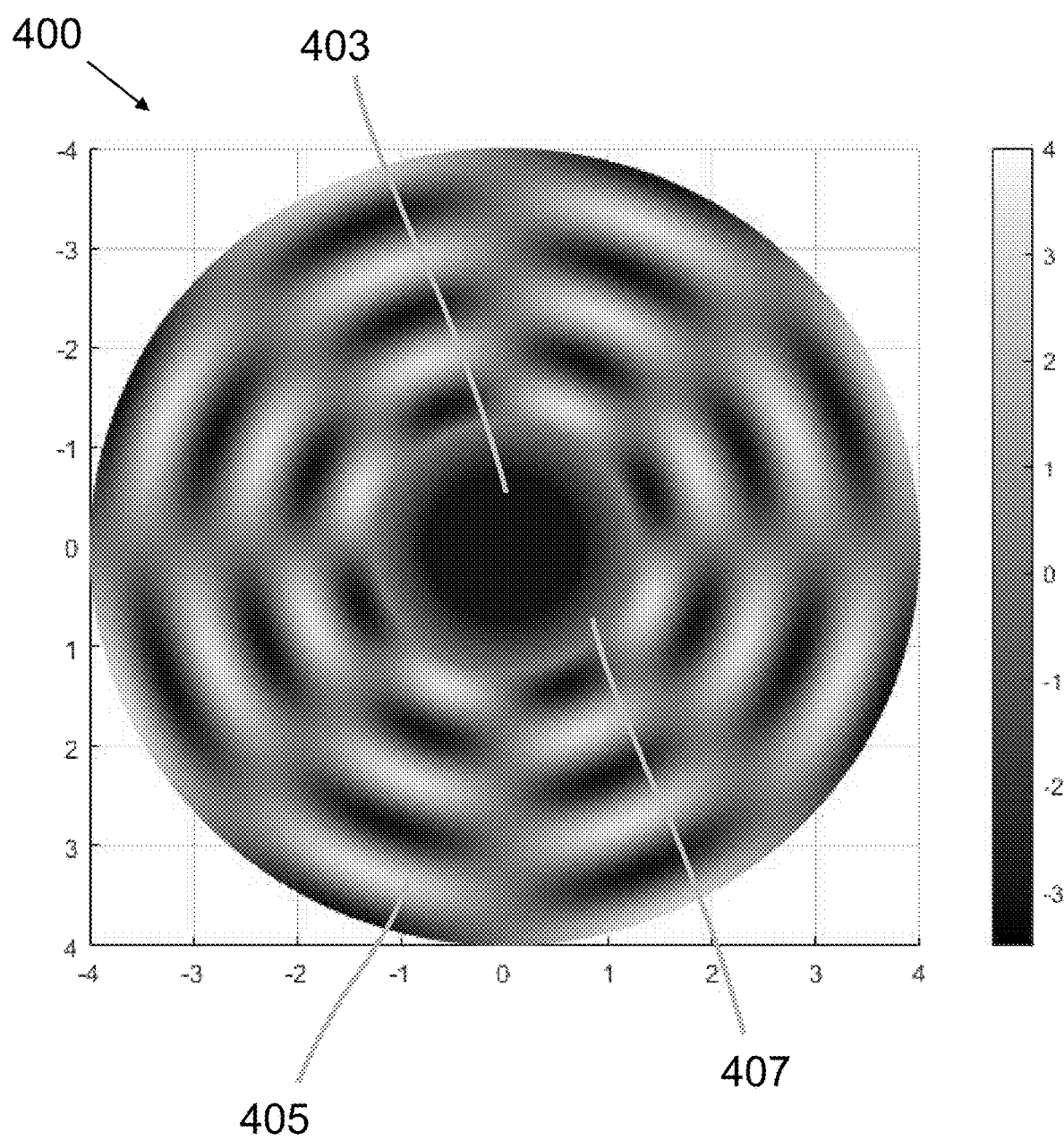
FIG. 5 shows a power map of an optic zone of a contact lens according to a second embodiment.

FIG. 5 shows a contact lens according to a second embodiment of the invention. The second embodiment is substantially the same as the first embodiment but the spiral provided by the second surface power map has been rotated through a 45 degree phase shift. As can be seen from FIG. 5, the superposition of first and second surface power maps comprising two counter-rotating spirals results in a similar pseudo-dartboard power map to that of the second embodiment. Thus, superposition of the two counter-rotating spirals results in a pseudo-dartboard lens power map irrespective of the relative phases of the first and second spirals. Once again, the overall lens power map of the contact lens 400 comprises a central region 403, an outer region 405, and a transition region 407.

Figure 7:
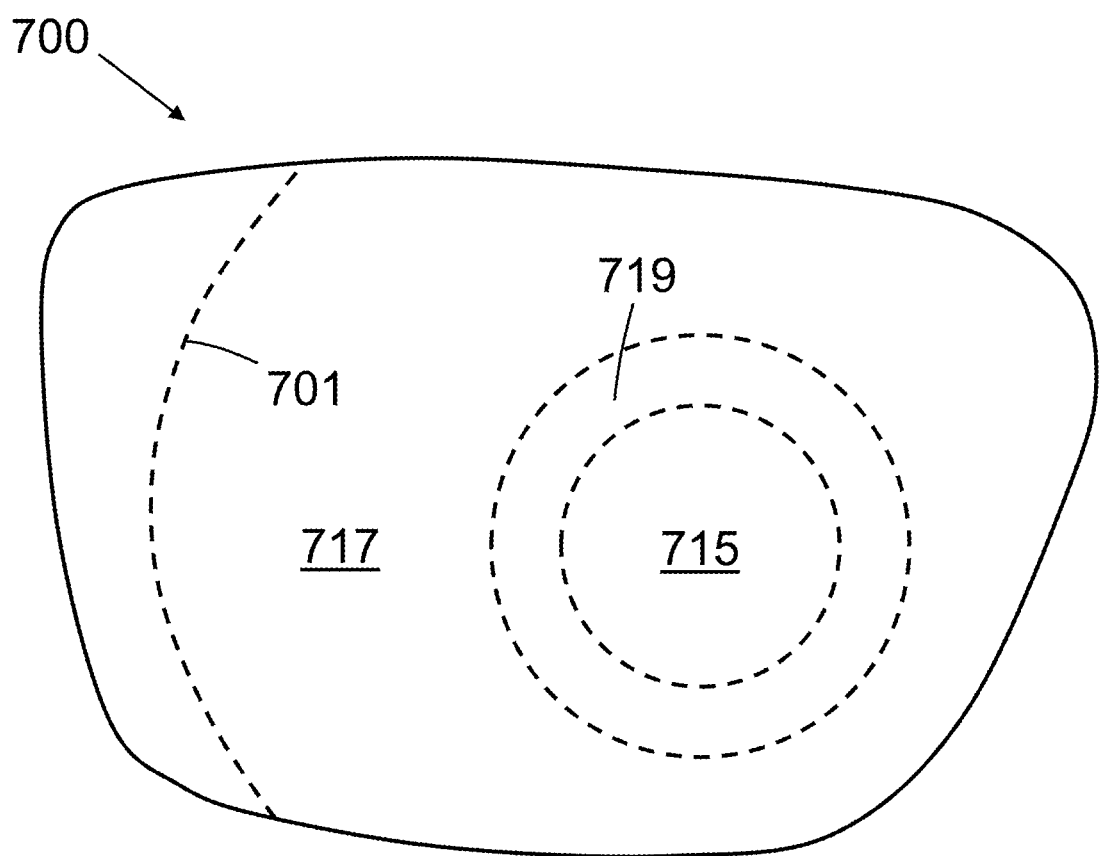
FIG. 7 shows a spectacle lens according to a third embodiment of the invention.

FIG. 7 shows a spectacle lens 700 according to a third embodiment of the invention. The spectacle lens comprises first and second surfaces providing first and second surface power maps substantially as described in respect of the first embodiment of the invention. It will, however, be appreciated by the skilled person that a spectacle lens does not comprise an optic zone in the same sense as the contact lens of the first embodiment. Therefore, in this case, the first and second surface power maps are provided by at least a portion of the spectacle lens, for example substantially all of the spectacle lens. It will be appreciated that alternative embodiments of the invention comprise spectacle lenses having surface power profiles substantially as described in respect of the second embodiment of the invention. Spectacle lens 700 comprises a central region 715, an outer region 717, and a transition region 719. In this example embodiment, the spirals formed by the first and second surface power maps do not extend to the left-most edge of the spectacle lens 717. Instead, the spirals only extend out to dashed line 701. It may be that the spirals decay in magnitude (for example, linearly) from the boundary between the transition region 719 and the outer region 717 as they extend outwards to dashed line 701. In other embodiments, the spirals may have substantially constant magnitude across the outer zone 717.

In such embodiments, the spectacle lens 700 may further comprise a narrow blending region running along dashed line 701. It will further be appreciated that, in other embodiments, the spirals continue outwards to the edges the spectacle lens 700. In this example embodiment, the central region 715 (and the surrounding transition region 719 and outer region 717) is not positioned in the geometric centre of the spectacle lens 700, and can be said to be offset from the geometric centre of the spectacle lens 700. It will be appreciated by the skilled person that such an offset may serve to place the central region in the part of the spectacle lens 700 through which a wearer most frequently looks.

According to a fourth embodiment of the invention, there is provided an intraocular lens. The intraocular lens comprises first and second surfaces providing first and second surface power maps substantially as described in respect of the first embodiment of the invention. It will be appreciated that alternative embodiments of the invention comprise intraocular lenses having surface power profiles substantially as described in respect of the second embodiment of the invention.

Figure 6:
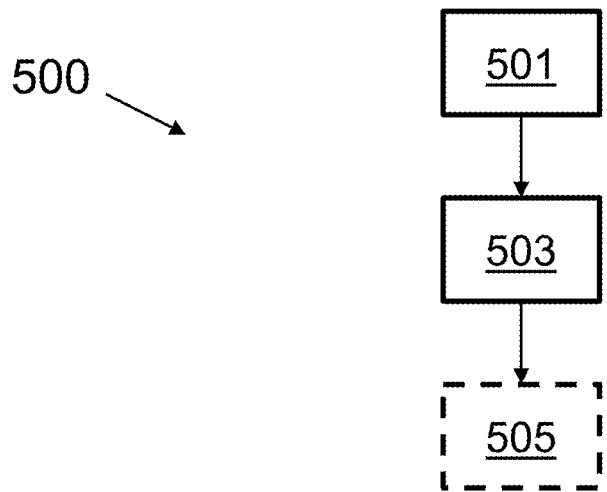
FIG. 6 shows a flow chart illustrating the steps of a method according to a fifth embodiment of the invention.

FIG. 6 shows a flow chart illustrating the steps of a method 500 of manufacturing a lens, for example a contact lens, for myopia control according to a fifth embodiment of the invention.

A first step of the method 500, represented by element 501, comprises operating a lathe to shape a first surface of one of: a lens, a mould for a lens, or an insert for manufacturing a mould for a lens. The first surface is shaped such that the first surface forms a first surface power map. The first surface power map comprises a spiral. It may be that the surface is shaped to vary substantially periodically both radially outwards from and angularly about an optical axis of the contact lens.

A second step of the method 500, represented by element 503, comprises operating a lathe to shape a second surface of the lens, the mould, or the insert. The second surface is shaped to form a second surface power map. The second surface power map comprises a spiral. It may be that the second surface is shaped to vary substantially periodically both radially outwards from and angularly about an optical axis of the contact lens. The second surface is shaped such that the spiral formed by the first surface power map twists in the opposite direction to that formed by the second surface power map.

When the first surface and the second surface are comprised on a mould for a lens or an insert for a mould for a lens, the method 500 may comprise an optional third step, represented by element 505. The third step 505 comprises using the mould of the insert for a mould for a lens to manufacture a lens.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

In both the first and second embodiments, the surface power maps of the contact lens each comprise a central region having substantially constant power, an outer region incorporating the spiral power profile, and a transition region providing a smooth transition between the central and outer regions. However, some alternative embodiments do not incorporate a transition region. Further alternative embodiments do not incorporate distinct central and outer regions. Instead, in such embodiments, the spiral profile extends from the centre of the each of the surface power maps all of the way out to the radial periphery of the surface power maps.

In the first and second embodiments, the spiral formed on the first surface power map twists in an anticlockwise direction and the spiral formed on the second surface power map twists in a clockwise direction. However, in alternative embodiments, the spiral formed on the first surface power map twists in a clockwise direction and the spiral formed on the second surface power map twists in an anti-clockwise direction.

In some embodiments of the invention, the spiral formed on one or both of the first and second surface power maps changes its direction of rotation at a pre-determined radial distance from the optical axis of the lens. For example, the spiral may rotate in a clockwise direction between the optical axis of the lens and the pre-determined radial distance, and in an anti-clockwise direction beyond the pre-determined radial distance. The lens may incorporate more than one change in the direction of rotation of the spiral. Thus, the spiral may, for example, change from a clockwise rotation to an anti-clockwise rotation before reverting to a clockwise rotation again. It will be appreciated by the skilled person that the lens can incorporate any number of changes in the direction of rotation of the spiral. It will also be appreciated that each of those changes in direction can take place at any chosen radial distance from the optical axis of the lens. The power map may therefore comprise annular rings alternating between clockwise and anti-clockwise rotating spirals. In such embodiments, it may be that each counter-rotating spiral changes its direction of rotation at the same radial distance from the optical axis of the lens.

In some embodiments, between regions of the ophthalmic lens having different directions of rotation, there may be a region in which the power map does not vary as a spiral. For example, the region may have a substantially constant power. For example, from the centre of the lens to a first radial distance, the lens may vary as a clockwise rotating spiral, followed by a region of substantially constant power, before varying as an anti-clockwise rotating spiral. The power map may therefore appear to comprise a plurality of annular rings, for example alternating between a spiral and substantially constant power, wherein the spiral regions also alternate between clockwise and anti-clockwise rotation.

Similarly, in some embodiments, the spiral may be interrupted by one or more regions, for example rings, in which the power map does not vary as a spiral. Such regions may have a substantially constant power. Thus, for example, the power map may comprise annular rings alternating between a spiral and substantially constant power. In such embodiments, the spiral may change its direction of rotation between each interruption, or it may continue with its previous direction of rotation. Thus, the spiral may maintain a constant direction of rotation across the lens, but may be interrupted by regions of substantially constant lens power.

Whilst embodiments of the invention have been described above in relation to a method of manufacturing contact lenses, moulds for contact lenses, or inserts for moulds for contact lenses using a lathe, it will be appreciated that other methods of manufacture are also possible. For example, the moulds or the inserts may also be manufactured using additive manufacturing techniques, for example by 3D printing.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. An ophthalmic lens for controlling progression of myopia, the lens including an outer surface that is convex, the outer surface shaped to form a first surface power map, and an inner surface that is concave, the inner surface shaped to form a second surface power map, wherein:
   the first surface power map comprises a spiral;
   the second surface power map comprises a spiral; and
   the spirals provided by the first and second surface power maps twist in opposing directions.

2. The ophthalmic lens according to claim 1, wherein the lens is a contact lens or a spectacle lens.

3. The ophthalmic lens according to claim 1, wherein the power varies smoothly across the first and second surface power maps.

4. The ophthalmic lens according to claim 3, wherein the power of the inner and outer surfaces varies both radially and angularly as a rounded square wave or a sinusoid.

5. The ophthalmic lens according to claim 1, wherein each of the first and second power maps has a power that varies substantially periodically both radially outwards from and angularly about an optical axis of the lens.

6. The ophthalmic lens according to claim 5, wherein the periods of the radial and angular variations are each substantially constant across the first and second surface power maps.

7. The ophthalmic lens according to claim 5, wherein a period of one or more of the radial and angular variations changes according to one or both of: a radial distance from the optical axis of the lens and an angular position about the optical axis of the lens.

8. The ophthalmic lens according to claim 5, wherein:
   the radial variation has a period of greater than 100 microns; and
   the angular variation has a period of greater than 6 degrees.

9. The ophthalmic lens according to claim 1, wherein the spirals formed on the first and second surface power maps twist in opposing directions but are otherwise substantially identical.

10. The ophthalmic lens according to claim 1, wherein each spiral comprises at least four arms.

11. The ophthalmic lens according to claim 1, wherein each arm of each spiral twists through at least half a rotation.

12. The ophthalmic lens according to claim 1, wherein:
   the lens comprises a central region and an outer region, the central region immediately surrounding the optical axis of the lens and the outer region surrounding the central region;
   the spirals are formed in the outer region; and
   the spirals do not extend into the central region.

13. The ophthalmic lens according to claim 12, wherein the central region has a diameter of less than 50% of that of the spirals.

14. The ophthalmic lens according to claim 12, wherein:
   the lens comprises a transition region, the transition region surrounding the central region and the outer region surrounding the transition region; and
   the power of the transition region varies to provide a smooth transition between the central and outer regions.

15. The ophthalmic lens according to claim 1, wherein:
   the lens comprises a central region and an outer region, the central region immediately surrounding the optical axis of the lens and the outer region surrounding the central region;
   the spirals are formed within the central region; and
   the spirals do not extend into the outer region.

16. A method of controlling myopia progression in a person, the method comprising:
   providing the multifocal ophthalmic lens according to claim 1 to a person in need of control of myopia progression.

17. The ophthalmic lens according to claim 1, wherein each spiral comprises a plurality of arms, and each of the plurality of arms comprises a peak arm and a trough arm.

18. A method of manufacturing an ophthalmic lens, the method comprising:
   operating a lathe to shape a concave surface and a convex surface of one of: a lens, a mould for a lens, or an insert for manufacturing a mould for a lens such that:
   the concave surface forms a first surface power map;
   the convex surface forms a second surface power map;
   the first surface power map and the second surface power map each comprise a spiral; and
   the spirals formed by the first surface power map and the second surface power map twist in opposing directions.

* * * * *